(12) United States Patent
Chauhan et al.

(10) Patent No.: US 6,946,154 B2
(45) Date of Patent: Sep. 20, 2005

(54) **PROCESS FOR PREPARING ANTIBACTERIAL AND ANTIOXIDANT FRACTION FROM SEABUCKTHORN (*HIPPOPHAE RHAMNOIDES* L.)**

(75) Inventors: Attar Singh Chauhan, Mysore (IN); Pradeep Singh Negi, Mysore (IN); Ramesh Shyam Ramteke, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,105

(22) Filed: Mar. 25, 2003

(65) Prior Publication Data

US 2004/0191340 A1 Sep. 30, 2004

(51) Int. Cl.$^7$ ............................................. A61K 35/78
(52) U.S. Cl. ....................... 424/776; 424/725; 424/405
(58) Field of Search ................................ 424/776, 725, 424/405

(56) References Cited

FOREIGN PATENT DOCUMENTS

| CN | 1089301 A | * | 7/1994 |
|---|---|---|---|
| RU | 2096040 A | * | 11/1997 |
| SU | 1275032 | | 12/1986 |
| SU | 1786064 A | * | 1/1993 |

OTHER PUBLICATIONS

Winterstein et al. Z. Physiol. Chem. 1932. vol. 207, pp. 25–34, CAPLUS Abstract enclosed.*

Velioglu et al. J. Agric. Food Chem. 1998. vol. 46, No. 10, pp. 4113–4117, FROSTI Abstract enclosed.*

English Abstract of SU 1275032 Dated: Dec. 7, 1986 (Database WPI—Derwent Publications, Ltd.) XP 002268596.

Isamukhamedov A, et al. "Hippophae Rhamnoides Seed Phospholipids" (1982) pp 395–396 (Database CA Online! Chemical Abstracts Service) XP009024685.

* cited by examiner

*Primary Examiner*—Christopher R. Tate
(74) *Attorney, Agent, or Firm*—Ladas and Parry LLP

(57) ABSTRACT

The present invention relates to a one step process for the preparation of antibacterial and antioxidant fraction from the unconventional parts of Seabuckthorn (*Hippophae rhamnoides* L.).

9 Claims, No Drawings

PROCESS FOR PREPARING ANTIBACTERIAL AND ANTIOXIDANT FRACTION FROM SEABUCKTHORN (*HIPPOPHAE RHAMNOIDES* L.)

FIELD OF THE INVENTION

The present invention relates to a one step process for the preparation of antibacterial and antioxidant fraction from the unconventional parts of Seabuckthorn (*Hippophae rhamnoides* L.).

BACKGROUND OF THE INVENTION

Spoilage of foods due to presence of bacterial and fungal infection has been a major concern for decades and it causes 50% loss worldwide [El-Ghaouth A. Journal of Industrial Microbiology and Biotechnology 1997; 19: 160]. The demand for non-toxic natural preservatives has been rising with increased awareness and reports of ill effects of synthetic chemicals present in foods. Many compounds present in berries has been reported to be biologically active, antimicrobial, allopathic, antioxidants and having bioregulatory properties such as tissue regeneration activities [Xu Mingyu et al. 1993. A brief report on antibacterial experiment using seabuckthorn. Seabuckthorn 6: 28–29]. Seabuckthorn berries have been reported to posses antibacterial, antioxidant, anti-inflammatory, antiallergenic and analgesic activity [Benavente-Garcia O, Castillo J, Martin F R, Ortuno A, Del Rio J A. Journal of Agriculture and Food Chemistry 1997; 45: 4505]. Seabuckthorn is widely grown plant which belongs to Elaeagnaceae family and genus *Hippophae*. It has been used in traditional Tibetan and Mangolian medicines (Lu Rongsen, 1992. Seabuckthorn: A multiple plant species for fragile mountains. International center for integrated mountain development, ICIMOD occasional paper No. 20, Kathmandu, Nepal). Seabuckthorn is known as wonder plant that bears small orange yellow to red colored fruits on two year old thorny twigs. The berry like fruit develops from an ovary or calyx tube, connected to ovary. Berries contain many bioactive substances and can be used in the treatment of several diseases like cardiovascular disease, cancer, acute mountain sickness etc. A total of more than 300 different medicine preparations involving seabuckthorn have been reported (Singh, 2001. International workshop on seabuckthorn, during 18–21 Feb. 2001, New Delhi).

Literature survey revealed that, there are no reports on the isolation of antibacterial and antioxidant fraction from the seeds of Seabuckthorn (*Hippophae rhamnoides* L.).

OBJECTS OF THE INVENTION

The main object of the present invention is to provide a one step process for preparation of a bioactive fraction, which has antibacterial and antioxidant activities. Hence, we have developed a process for the preparation of bioactive fraction from the unconventional parts of Seabuckthorn (*Hippophae rhamnoides* L.), to which no commercial value has been attributed so far.

Another object of the present invention is to provide a technology for the preparation of an antibacterial and antioxidant fraction from the unconventional parts of Seabuckthorn (*Hippophae rhamnoides* L.), which can be used as potential natural preservative.

Yet another object of the present invention is to provide an efficient process for the large-scale preparation of antibacterial and antioxidant fraction from the unconventional parts of Seabuckthorn (*Hippophae rhamnoides* L.).

Still another object of the present invention is to provide a one step process for the preparation of antibacterial and antioxidant fraction from the unconventional parts of Seabuckthorn (*Hippophae rhamnoides* L.).

It is another object of the invention to provide an efficient process using simple extraction methods and solvents, which can be re-used for the preparation of antibacterial and antioxidant fraction from Seabuckthorn.

SUMMARY OF THE INVENTION

Accordingly, the present invention provides the one step process for the preparation of antibacterial and antioxidant fraction, which comprises washing the seeds of seabuckthorn (*Hippophae rhamnoides* L.) with tap water in order to remove any dirt or extraneous matter followed by drying at 40–50° C. for a residence period of 3–4 hours; powdering the seeds of Seabuckthorn (*Hippophae rhamnoides* L.) to get a particle size of 60–80 mesh; extracting of the above said material with leotropic series solvents (Elution effect in increasing order) followed by methanol in a Soxhlet extractor at a temperature of 55–60° C. for a period of 8–9 hours; filtering the above extract using Whatman filter paper no.41 to obtain the particle free extract; distilling the above extract in distillation unit at 60–65° C. to recover the solvent up to 80–90%, which is further recycled for further extraction in soxhlet unit; concentrating the above particle free extract under vacuum by employing 200–250 mbar pressure in flash evaporator at a temperature of 45–50° C. to get crude extract of methanol; drying the above concentrated crude extract either by freeze drying for antioxidant activity or under vacuum by employing 175–200 mbar pressure in vacuum oven at 40–50 ° C. for a residency period of 8–9 hours for antibacterial activity.

The dried product thus obtained had antibacterial activity in terms of minimum inhibitory concentration ($\mu$g/ml) against different Gram positive and Gram negative bacteria in the range of 200–350 and antioxidant activity in terms of % radical scavenging activity in the range of 40.379–93.473 at 10–50 $\mu$g/ml concentration respectively as determined by DPPH method.

In an embodiment of the present invention, the rotation of the flask containing methanol extract of seabuckthorn seeds is used for concentration in flash evaporator at 80–100 rpm under vacuum of 200–250 mbar by employing 60–65° C. temperature.

In another embodiment of the present invention, the yield of methanol extract was found to be 14.264 g/100 g after freeze-drying and 14.4858 g/100 g after vacuum drying.

DETAILED DESCRIPTION OF THE INVENTION

The process of the present invention involves following steps, which comprises of:

i) Washing the seeds of seabuckthorn (*Hippophae rhamnoides* L.) with tap water in order to remove any dirt or extraneous matter followed by drying at 40–50° C. for a residence period of 3–4 hours.

ii) Powdering the seeds of Seabuckthorn (*Hippophae rhamnoides* L.) to get a particle size of 60–80 mesh.

iii) Extracting of the above said material with leotropic series solvents (Elution effect in increasing order) followed by methanol in a Soxhlet extractor at a temperature of 55–60° C. for a period of 8–9 hours.

iv) Filtering above extract using Whatman filter paper no.41 to obtain particle free extract.
v) Distilling the above extract in distillation unit at 60–65° C. to recover the solvent up to 80–90%, which is further recycled for further extraction in soxhlet unit.
vi) Concentrating the above particle free extract under vacuum by employing 200–250 mbar pressure in flash evaporator at a temperature of 45–50° C. in order to get crude extract of methanol.
vii) Drying the above concentrated crude extract either by freeze dying for antioxidant activity or under vacuum by employing 175–200 mbar pressure in vacuum oven at 40–50° C. for a residency period of 8–9 hours for antibacterial activity.

The dried product thus obtained had antibacterial activity in terms of minimum inhibitory concentration ($\mu$g/ml) against different Gram positive and Gram negative bacteria in the range of 200–350 and antioxidant activity in terms of % radical scavenging activity in the range of 40,379–93.473 by using 10–50 $\mu$g/ml concentration respectively as determined by DPPH method.

The preparation of antibacterial factions from the unconventional parts of Seabuckthorn (*Hippophae rhamnoides L.*) was done according to following process flow:

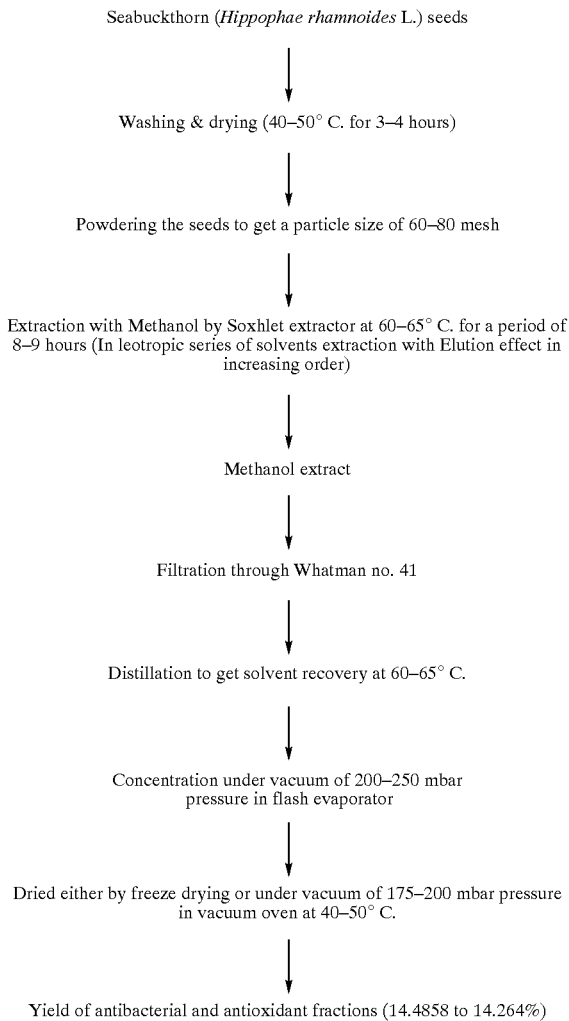

Seabuckthorn (*Hippophae rhamnoides* L.) seeds
↓
Washing & drying (40–50° C. for 3–4 hours)
↓
Powdering the seeds to get a particle size of 60–80 mesh
↓
Extraction with Methanol by Soxhlet extractor at 60–65° C. for a period of 8–9 hours (In leotropic series of solvents extraction with Elution effect in increasing order)
↓
Methanol extract
↓
Filtration through Whatman no. 41
↓
Distillation to get solvent recovery at 60–65° C.
↓
Concentration under vacuum of 200–250 mbar pressure in flash evaporator
↓
Dried either by freeze drying or under vacuum of 175–200 mbar pressure in vacuum oven at 40–50° C.
↓
Yield of antibacterial and antioxidant fractions (14.4858 to 14.264%)

The Novelty of the Process is:
1. This is the first report of preparation of antibacterial and antioxidant fraction from the unconventional parts of Seabuckthorn (*Hippophae rhamnoides L.*).
2. The invention is a one step process to obtain the bioactive fraction from the unconventional parts of Seabuckthorn (*Hippophae rhamnoides L.*).

The following examples are given by way of illustration of the present invention and therefore should not be construed to limit the scope of the present invention. Variations and changes may be made by one skilled in the art without departing from the spirit of the invention. All parts and percentages are by weight, unless otherwise indicated.

EXAMPLE 1

100 g seeds of Seabuckthorn (*Hippophae rhamnoides L.*) were washed and dried in vacuum oven (pressure 175) at 40° C. for 4 hours followed by powdering in mixer grinder at 18000 rpm to get a 60 mesh size powder particle. The powder was extracted using 200 ml of methanol at 60° C. for 8 h in a Soxhlet extractor. The methanol extract was filtered using Whatman filter paper No.41 in order to get clear extract and it was distilled at 60° C. by using distillation unit to recover the 160 ml of solvent. The crude extract was concentrated under vacuum of 200 mbar pressure and flask rotation speed of 100 rpm was maintained in flash evaporator for a period of 2 hours and it was dried using freeze drying technique for the residency period of 6 hours for antioxidant activity determination and dried under vacuum for antibacterial activity at 175 mbar pressure for the residency period of 9 hours in a vacuum oven at 40° C. The yield of the freeze-dried methanol extract for antioxidant activity and vacuum oven dried menthol extract for antibacterial assay were 14.264 g and 14.4858 g, respectively. Free radical-scavenging activity of each antioxidant was assayed using a stable free radical, DPPH (1,1-Diphenyl-2-picrylhydrazyl), according to the method of Blois (Blois, 1958. Antioxidant determinations by the use of a stable free radical . Nature, 181: 1199–1200). The reaction mixture contained 0.5 ml of 0.5 mM DPPH and 0.1 ml of dimethyl sulphoxide containing the antioxidant extract at different concentrations (10–50 $\mu$g). Finally, the total volume of the reaction mixture was adjusted to 1.0 ml by adding 100 mM Tris-HCl buffer (pH7.4). After the reaction was carried out at room temperature for 20 minutes in the dark, the radical-scavenging activity of each antioxidant was quantified by decolorisation at 517 nm. The % radical scavenging activity on DPPH for the 10 $\mu$g/ml was 40.379. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred $\mu$l (about $10^3$ cfu/ml) of culture was inoculated into the flasks under aseptic conditions. The media was then poured into sterilized petri plates in quadruplet and incubated at 37° C. for 24 h for growth. The minimum inhibitory concentration (MIC) was reported as the lowest concentration of the compound capable of inhibiting the complete growth of the bacterium being tested. The MIC value of Seabuckthorn (*Hippophae rhamnoides L.*) seed extract against *Bacillus cereus* was 200 ppm.

EXAMPLE-2

100 g seeds of Seabuckthorn (*Hippophae rhamnoides L.*) were washed and dried in vacuum oven (pressure 180 mbar) at 40° C. for 3 hours followed by powdering in mixer grinder at 18000 rpm to get a 70 mesh size powder particle. The powder was extracted using 200 ml of methanol at 55° C. for 9 h in a Soxhlet extractor. The methanol extract was filtered using Whatman filter paper No.41 in order to get clear extract and it was distilled at 65° C. by using distillation unit to recover the 170 ml of solvent. The crude extract was concentrated under vacuum of 250 mbar pressure and flask rotation speed of 100 rpm was maintained in flash evaporator for a period of 2 hours and it was dried using freeze drying technique for the residency period of 6 hours and also dried under vacuum of 200 mbar for the residency period of 8 hours in a vacuum oven at 50° C. The yield of the freeze-dried methanol extract for antioxidant activity and vacuum oven dried methanol extract for antibacterial assay were 14.264 g and 14.4858 g, respectively. Free radical-scavenging activity of each antioxidant was assayed using a stable free radical, DPPH (1,1-Diphenyl-2-picrylhydrazyl), according to the method of Blois (Blois, 1958. Antioxidant determinations by the use of a stable free radical. Nature, 181: 1199–1200). The reaction mixture contained 0.5 ml of 0.5 mM DPPH and 0.1 ml of dimethyl sulphoxide containing the antioxidant extract at different concentrations (10–50 µg). Finally, the total volume of the reaction mixture was adjusted to 1.0 ml by adding 100 nM Tris-HCl buffer (pH7.4). After the reaction was carried out at room temperature for 20 minutes in the dark, the radical-scavenging activity of each antioxidant was quantified by decolorisation at 517 nm. The % radical scavenging activity on DPPH for the 20 µg/ml was 71.2277. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred µl (about $10^3$ cfu/ml) of culture was inoculated into the flasks under aseptic conditions. The media was then poured into sterilized petri plates in quadruplet and incubated at 37° C. for 20 h for growth. The minimum inhibitory concentration (MIC) was reported as the lowest concentration of the compound capable of inhibiting the complete growth of the bacterium being tested. The MIC value of Seabuckthorn (*Hippophae rhamnoides L.*) seed extract against *Bacillus subtilis* was 300 ppm.

EXAMPLE-3

100 g seeds of Seabuckthorn (*Hippophae rhamnoides L.*) were washed and dried in vacuum oven (pressure 200 mbar) at 45° C. for 3 hours followed by powdering in mixer grinder at 18000 rpm to get a 80 mesh size powder particle. The powder was extracted using 200 ml of menthol at 60° C. for 8 h in a Soxhlet extractor. The methanol extract was filtered using Whatman filter paper No.41 in order to get clear extract and it was distilled at 60° C. by using distillation unit to recover the 175 ml of solvent. The crude extract was concentrated under vacuum of 200–250 mbar pressure and flask rotation speed of 100 rpm was maintained in flash evaporator for a period of 2 hours and it was dried using freeze drying technique for the residency period of 6 hours and also dried under vacuum of 175–200 mbar for the residency period of 8 hours in a vacuum oven at 40° C. The yield of the freeze-dried methanol extract for antioxidant activity and vacuum oven dried methanol extract for antibacterial assay were 14.264 g and 14.4858 g, respectively. Free radical-scavenging activity of each antioxidant was assayed using a stable free radical, DPPH (1,1-Diphenyl-2-picrylhydrazyl), according to the method of Blois (Blois, 1958. Antioxidant determinations by the use of a stable free radical . Nature, 181: 1199–1200). The reaction mixture contained 0.5 ml of 0.5 mM DPPH and 0.1 ml of dimethyl sulphoxide containing the antioxidant extract at different concentrations (10–50 µg). Finally, the total volume of the reaction mixture was adjusted to 1.0 ml by adding 100 mM Tris-HCl buffer (pH7.4). After the reaction was carried out at room temperature for 20 minutes in the dark, the radical-scavenging activity of each antioxidant was quantified by decolorisation at 517 nm. The % radical scavenging activity on DPPH for the 30 µg/ml was 85.1777. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred µl (about $10^3$ cfu/ml) of culture was inoculated into the flasks under aseptic conditions. The media was then poured into sterilized petri plates in quadruplet and incubated at 37° C. for 22 h for growth. The minimum inhibitory concentration (MIC) was reported as the lowest concentration of the compound capable of inhibiting the complete growth of the bacterium being tested. The MIC value of Seabuckthorn (*Hippophae rhamnoides L.*) seed extract against *Bacillus coagulans* was 300 ppm.

EXAMPLE 4

100 g seeds of Seabuckthorn (*Hippophae rhamnoides L.*) were washed and dried in vacuum oven (pressure 200 mbar) at 50° C. for 3 hours followed by powdering powdered using mixer grinder at 18000 rpm to get a 80 mesh size powder particle. The powder was extracted using 200 ml of methanol at 60° C. for 8 h in a Soxhlet extractor. The methanol extract was filtered using Whatman filter paper No.41 in order to get clear extract and it was distilled at 60° C. by using distillation unit to recover the 175 ml of solvent. The crude Fact was concentrated wider vacuum of 250 mbar pressure and flask rotation speed of 100 rpm was maintained in flash evaporator for a period of 2 hours and it was dried using freeze drying technique for the residency period of 6 hours and also dried under vacuum of 200 mbar for the residency period of 8 hours in a vacuum oven at 40° C. The yield of the freeze-dried methanol extract for antioxidant activity and vacuum oven dried methanol extract for antibacterial assay were 14.264 g and 14.4858 g, respectively. Free radical-scavenging activity of each antioxidant was assayed using a stable free radical, DPPH (1,1-Diphenyl-2-picrylhydrazyl), according to the method of Blois (Blois, 1958. Antioxidant determinations by the use of a stable free radical. Nature, 181: 1199–1200). The reaction mixture contained 0.5 ml of 0.5 mM DPPH and 0.1 ml of dimethyl sulphoxide containing the antioxidant extract at different concentrations (10–50 µg). Finally, the total volume of the reaction mixture was adjusted to 1.0 ml by add 100 mM Tris-HCl buffer pH7.4). After the reaction was carried out at room temperature for 20 minutes in the dark, the radical-scavenging activity of each antioxidant was quantified by decolorisation at 517 nm. The % radical scavenging activity on DPPH for the 40 µg/ml was 92.2185. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred μl (about $10^3$ cfu/ml) of culture was inoculated into the flasks under aseptic conditions. The media was then poured into sterilized petri plates in quadruplet and incubated at 37° C. for 20 h for growth. The minimum inhibitory concentration (MIC) was reported as the lowest concentration of the compound capable of inhibiting the complete growth of the bacterium being tested. The MIC value of Seabuckthorn (*Hippophae rhamnoides L.*) seed extract against *Pseudomonas aeruginosa* was 300 ppm.

EXAMPLE 5

100 g seeds of Seabuckthorn (*Hippophae rhamnoides L.*) were washed and dried in vacuum oven (pressure 200 mbar) at 50° C. for 3 hours followed by powdering in mixer grinder at 18000 rpm to get a 60 mesh size powder particle. The powder was extracted using 200 ml of methanol at 60° C. for 8 h in a Soxhlet extractor. The methanol extract was filtered using Whatman filter paper No.41 in order to get clear extract and it was distilled at 65° C. by using distillation unit to recover the 180 ml of solvent. The crude extract was concentrated under vacuum of 250 mbar pressure and flask rotation speed of 100 rpm was maintained in flash evaporator for a period of 2 hours and it was dried using freeze drying technique for the residency period of 6 hours and also dried under vacuum of 200 mbar for the residency period of 8 hours in a vacuum oven at 50° C. The yield of the freeze-dried methanol extract for antioxidant activity and vacuum oven dried methanol extract for antibacterial assay were 14.264 g and 14.4858 g, respectively. Free radical-scavenging activity of each antioxidant was assayed using a stable free radical, DPPH (1,1-Diphenyl-2-picrylhydrazyl), according to the method of Blois (Blois, 1958. Antioxidant determinations by the use of a stable free radical . Nature, 181: 1199–1200). The reaction mixture contained 0.5 ml of 0.5 mM DPPH and 0.1 ml of dimethyl sulphoxide containing the antioxidant extract at different concentrations (10–50 μg). Finally, the total volume of the reaction mixture was adjusted to 1.0 ml by adding 100 mM Tris-HCl buffer (pH7.4). After the reaction was carried out at room temperature for 20 minutes in the dark, the radical-scavenging activity of each antioxidant was quantified by decolorisation at 517 nm. The % radical scavenging activity on DPPH for the 50 μg/ml was 93.473. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred μl (about $10^3$ cfu/ml) of culture was inoculated into the flasks under aseptic conditions. The media was then poured into sterilized petri plates in quadruplet and incubated at 37° C. for 20 h for growth. The minimum inhibitory concentration (MIC) was reported as the lowest concentration of the compound capable of inhibiting the complete growth of the bacterium being tested. The MIC value of Seabuckthorn (*Hippophae rhamnoides L.*) seed extract against *Listeria monocytogenes* was 300 ppm.

EXAMPLE 6

100 g seeds of Seabuckthorn (*Hippophae rhamnoides L.*) were washed and dried in vacuum oven (pressure 200 mbar) at 40° C. for 3 hours followed by powdering powdered using mixer grinder at 18000 rpm to get a 60 mesh size powder particle, The powder was extracted using 200 ml of menthol at 60° C. for 8 h in a Soxhlet extractor. The methanol extract was filtered using Whatman filter paper No.41 in order to get clear extract and it was distilled at 60° C. by using distillation unit to recover the 180 ml of solvent. The crude extract was concentrated under vacuum of 200 mbar pressure and flask rotation speed of 100 rpm was maintained in flash evaporator for a period of 2 hours and it was dried using freeze drying technique for the residency period of 6 hours and also dried under vacuum of 175 mbar for the residency period of 9 hours in a vacuum oven at 40° C. The yield of the freeze-dried methanol extract for antioxidant activity and vacuum oven dried methanol extract for antibacterial assay were 14.264 g and 14.4858 g, respectively. The antibacterial assay for the extract of Seabuckthorn (*Hippophae rhamnoides L.*) was tested by pour plate method against *Bacillus cereus* by the method of Negi et al. (J. Agricultural and Food Chemistry 47, 4297–4300, 1999). To flasks containing 20 ml melted nutrient agar, different concentration of test material in propylene glycol were added. Equivalent amounts of propylene glycol were used as controls. One hundred μl (about $10^3$ cfu/ml) of culture was inoculated into the flasks under aseptic conditions. The media was then poured into sterilized pet plates in quadruplet and incubated at 37° C. for 24 h for growth. The minimum inhibitory concentration (MIC) was reported as the lowest concentration of the compound capable of inhibiting the complete growth of the bacterium being tested, The MIC value of Seabuckthorn (*Hippophae rhamnoides L.*) seed extract against *Yersinia enterocolitica* was 350 ppm.

The Advantages of the Process is

1. The process is simple and the solvents used in this process can be regenerated for further use.
2. The raw material (seed) has no commercial value at present.

We claim:

1. A process for preparing a crude extract having antibacterial and/or antioxidant activity from Seabuckthorn (*Hippophae rhamnoides L.*) which comprises:
   i) washing the seeds of Seabuckthorn (*Hippophae rhamnoides L.*) with water to remove any dirt or extraneous matter followed by drying;
   ii) powdering the dried seeds to obtain a particle size of 60–80 mesh;
   iii) extracting the powdered dried seeds with methanol in a Soxhlet extractor to obtain an extract;
   iv) filtering the extract to remove any particles and obtain a particle free extract;
   v) distilling the particle free extract to recover methanol;
   vi) concentrating the distilled particle free extract under vacuum to obtain a concentrated extract;
   vii) drying the concentrated crude extract to obtain an extract with antibacterial activity and/or antioxidant activity.

2. A process as claimed in claim 1 wherein the seeds of Seabuckthorn are washed with tap water and then dried at 40–50° C. for a residence period of 3–4 hours.

3. A process as claimed in claim 1 wherein the extraction of the powdered seeds is done in a Soxhlet extractor at a temperature of 55–60° C. for a period of 8–9 hours.

4. A process as claimed in claim 1 wherein the filtering of the extract is done using Whatman filter paper no. 41.

5. A process as claimed in claim 1 wherein the distillation is done in a distillation unit at 60–65° C. to recover 80–90% of the methanol.

6. A process as claimed in claim 5 wherein the recovered methanol is recycled for use in extraction to the Soxhlet unit.

7. A process as claimed in claim 1 wherein the particle free extract is concentrated under vacuum using 200–250 mbar pressure in flash evaporator at a temperature of 45–50° C. to obtain the crude extract.

8. A process as claimed in claim 1 wherein the drying of the concentrated crude extract is done by freeze drying.

9. A process as claimed in claim 1 wherein the drying of the concentrated crude extract is done under a vacuum by employing 175–200 mbar pressure in a vacuum oven at 40–50° C. for a residency period of 8–9 hours.

* * * * *